(12) United States Patent
Miller (10) Patent No.: US 9,232,994 B2
(45) Date of Patent: Jan. 12, 2016

(54) STENTED PROSTHETIC HEART VALVE AND METHODS FOR MAKING

(71) Applicant: Medtronic Ventor Technologies Ltd., Netanya (IL)

(72) Inventor: Noam Miller, Netanya (IL)

(73) Assignee: Medtronic Vascular Galway Limited, Ballybrit, Galway (IE)

( * ) Notice: Subject to any disclaimer, the term of this patent is extended or adjusted under 35 U.S.C. 154(b) by 225 days.

(21) Appl. No.: 13/833,436

(22) Filed: Mar. 15, 2013

(65) Prior Publication Data

US 2014/0277418 A1    Sep. 18, 2014

(51) Int. Cl.
*A61F 2/24*    (2006.01)

(52) U.S. Cl.
CPC ............. *A61F 2/2403* (2013.01); *A61F 2/2412* (2013.01); *A61F 2/2415* (2013.01); *A61F 2220/0075* (2013.01)

(58) Field of Classification Search
CPC ....... A61F 2/24; A61F 2/2412; A61F 2/2415; A61F 2/2418; A61F 2/2403; A61F 2/2406
USPC ............. 623/1.26, 2.1, 2.12, 2.13, 2.14, 2.15, 623/2.16, 2.17, 2.18, 2.19, 23.7
See application file for complete search history.

(56) References Cited

U.S. PATENT DOCUMENTS

| | | | |
|---|---|---|---|
| 8,052,750 B2 | 11/2011 | Tuval et al. | |
| 2008/0004688 A1* | 1/2008 | Spenser et al. | 623/1.13 |
| 2008/0071361 A1 | 3/2008 | Tuval et al. | |
| 2009/0240320 A1* | 9/2009 | Tuval et al. | 623/1.24 |
| 2009/0292350 A1 | 11/2009 | Eberhardt et al. | |
| 2010/0018447 A1 | 1/2010 | Holecek et al. | |
| 2010/0023120 A1* | 1/2010 | Holecek et al. | 623/2.19 |
| 2010/0049313 A1 | 2/2010 | Alon et al. | |
| 2011/0224780 A1 | 9/2011 | Tabor et al. | |
| 2011/0251675 A1 | 10/2011 | Dwork | |
| 2011/0295363 A1 | 12/2011 | Girard et al. | |
| 2012/0059454 A1 | 3/2012 | Millwee et al. | |
| 2012/0083879 A1 | 4/2012 | Eberhardt et al. | |
| 2012/0137521 A1 | 6/2012 | Millwee et al. | |
| 2012/0158129 A1 | 6/2012 | Duffy et al. | |

FOREIGN PATENT DOCUMENTS

WO    WO03/047468    6/2006

OTHER PUBLICATIONS

PCT/US2014/021268, PCT Search Report and Written Opinion, mailed Jun. 3, 2014.

* cited by examiner

*Primary Examiner* — Christopher D Prone
*Assistant Examiner* — Rokhaya Diop (57) ABSTRACT

A stented prosthetic heart valve including a stent, a plurality of leaflets, and a coupling apparatus. The stent includes a plurality of struts combining to define a generally tubular body, with the struts forming strut segments. The leaflets are mounted to the stent, and include a leaflet provided as part of a first leaflet layer that further forms a tab region. The coupling apparatus is configured for connecting the first leaflet layer to the stent, and includes a backing layer, a guide plate, and a pin. The guide plate and the pin are formed apart from the stent. In this regard, a portion of the backing layer and the tab region are secured between the guide plate and the pin. Further, another portion of the backing layer is attached to at least one of the strut segments to mount the leaflet of the first leaflet layer to the stent.

18 Claims, 12 Drawing Sheets

STENTED PROSTHETIC HEART VALVE AND METHODS FOR MAKING

BACKGROUND

The present disclosure relates to prosthetic heart valves. More particularly, it relates to stented prosthetic heart valves and methods for making the same.

All four of the valves in the heart are passive structures in that they do not themselves expend any energy and do not perform any active contractile function. They consist of moveable "leaflets" that open and close in response to differential pressures on either side of the valve. The problems that can develop with valves can generally be classified into two categories: (1) stenosis, in which a valve does not open properly, and (2) insufficiency (also called regurgitation), in which a valve does not close properly. Stenosis and insufficiency may occur concomitantly in the same valve or in different valves. Both of these abnormalities increase the workload placed on the heart. The severity of this increased stress on the heart and the patient, and the heart's ability to adapt to it, determine the treatment options that can be pursued. In some cases, medication can be sufficient to treat the patient, which is the preferred alternative; however, in many cases defective valves have to repaired or completely replaced in order for the patient to live a normal life.

The two general categories of valves that are available for implantation into the cardiac system are mechanical valves and bioprosthetic or tissue valves. Mechanical valves have been used for many years and encompass a wide variety of designs that accommodate the blood flow requirements of the particular location where they will be implanted. Although the materials and design features of these valves are continuously being improved, they may increase the risk of clotting in the blood stream, which can lead to a heart attack or stroke. Thus, mechanical valve recipients must take anti-coagulant drugs for life to lessen the potential for blood clot formation. Further, mechanical valves can sometimes suffer from structural problems that may force the patient to have additional surgeries for further valve replacement.

Bioprosthetic valves, which are also referred to as prosthetic valves, generally include both human tissue valves and animal tissue valves. The designs of these bioprosthetic valves are typically relatively similar to the design of the natural valves of the patient and advantageously do not require the use of long-term anti-coagulant drugs. Animal tissue valves are widely available to patients who require valve replacement. The most common types of animal tissue valves used include porcine aortic valves, and bovine and porcine pericardial valves.

In general terms, prosthetic heart valve fabrication requires leaflets to be cut in a predetermined geometry from animal-derivative tissue (e.g., porcine pericardium) and then sewn or otherwise connected together. In many instances the cut leaflets are mounted to a frame, such as a metal stent. A number of different techniques and methods have been used to incorporate the tissue valve leaflets to the stent, such as clamping, tying, gluing, or stitching, for example. Many of the techniques used for this purpose generally produce a stented prosthetic heart valve that has concentrated stresses at the points where the leaflets are attached to the stent frame. That is, because the stents are relatively rigid as compared to the flexible material from which the leaflets of the tissue valve are made, the repetitive flexing motion of the leaflets can create stress concentrations at the points where the tissue valve is attached to the stent. Further, the stent typically must incorporate special design features (e.g., unique slots that serve as commissure connection points) solely for attachment of the tissue leaflets, in manner that orients the coaptation edges of the leaflets in an aligned arrangement.

In light of the above, a need exists for methods and devices for a durable attachment between a tissue valve and a stent in the manufacture of a stented prosthetic heart valve.

SUMMARY

Some aspects in accordance with principles of the present disclosure relate to a stented prosthetic heart valve including a stent, a plurality of leaflets, and a coupling apparatus. The stent includes a plurality of struts combining to define a generally tubular body, with the struts forming strut segments. The leaflets are mounted to the stent, and include a leaflet provided as part of a first leaflet layer that further forms a tab region. The coupling apparatus is configured for connecting the first leaflet layer to the stent, and includes a backing layer, a guide plate, and a pin. The guide plate and the pin are formed apart from the stent. In this regard, a portion of the backing layer and the tab region are secured between the guide plate and the pin. Further, another portion of the backing layer is attached to at least one of the strut segments to mount the leaflet of the first leaflet layer to the stent. In some embodiments, a second leaflet layer that forms another one of the leaflets as well as a tab region is also provided, and the coupling apparatus includes a second backing layer. The tab regions of the first and second leaflet layers are sandwiched between a base provided with each of the backing layers, with the combined assembly being assembled to the guide plate and the pin. Further, flaps provided with each of the backing layers are wrapped about separate strut segments in securing the first and second leaflet layers to the stent. In some embodiments, the strut segment(s) to which the backing layer(s) is attached are part of a stent cell; the coupling apparatus is configured for straightforward assembly to the stent cell while arranging the free edge of the corresponding leaflet(s) in a desired orientation across the stent.

Other aspects in accordance with principles of the present disclosure relate to a stented prosthetic heart valve including a stent and a plurality of leaflet assemblies. The stent includes a plurality of struts combining to define a generally tubular body, with the struts forming strut segments. The leaflet assemblies are mounted to the stent, and at least one of the leaflet assemblies includes two backing layers and two leaflet layers. Each of the backing layers includes a base and a flap. Each of the leaflet layers includes a leaflet and a tab region. The tab regions of the leaflet layers are affixed between the bases. The flap of the first backing layer is attached to a first strut segment, and the flap of the second backing layer is attached to a second strut segment. In this regard, the first and second strut segments are part of a cell formed by the stent.

Yet other aspects in accordance with principles of the present disclosure relate to a method of manufacturing a stented prosthetic heart valve. The method includes securing a leaflet layer to a backing layer at an interface between a guide plate and a pin. The backing layer is attached to a strut segment of a stent to provide a leaflet assembly affixed to the stent. In this regard, the stent includes a plurality of struts that combine to define a tubular body. The guide plate and the pin are independent of the struts comprising the stent. In some embodiments, the step of securing the leaflet layer to the backing layer includes inserting a tab region of the leaflet layer and a base of the backing layer through a passageway defined by the guide plate. The tab region and the base are lodged between the pin and the guide plate. The pin and guide plate are then connected to frictionally secure the tab region and the base to one another in an abutting relationship. In yet other embodiments, the backing layer further includes a flap projection from the base, and the flap is wrapped about the strut segment.

BRIEF DESCRIPTION OF THE DRAWINGS

FIGS. 8-9B illustrate mounting of the leaflet assembly of FIG. 3 to a stent.

DETAILED DESCRIPTION

Prosthetic heart valves of the present disclosure can be used for replacement of pulmonary valves, aortic valves, mitral valves, or tricuspid valves, in accordance with the methods and valve constructions of the present disclosure. The prosthetic heart valves of the present disclosure can be compressible to a reduced diameter during the implantation process, such as for transcatheter implantation, and can be capable of being expanded (e.g., self-expanding, balloon expanded, etc.) to a larger diameter once they are in their desired implantation location. The prosthetic heart valves can be used as a surgical sutureless or apical implant, or can be utilized in percutaneous replacement of cardiac valves, for example. One exemplary method for assembling a stented prosthetic heart valve of the present disclosure generally includes the manufacture and preparation of a valve segment, then a subsequent mounting or attachment of the prepared segment to a stent, which is described in further detail below.

Figure 1:
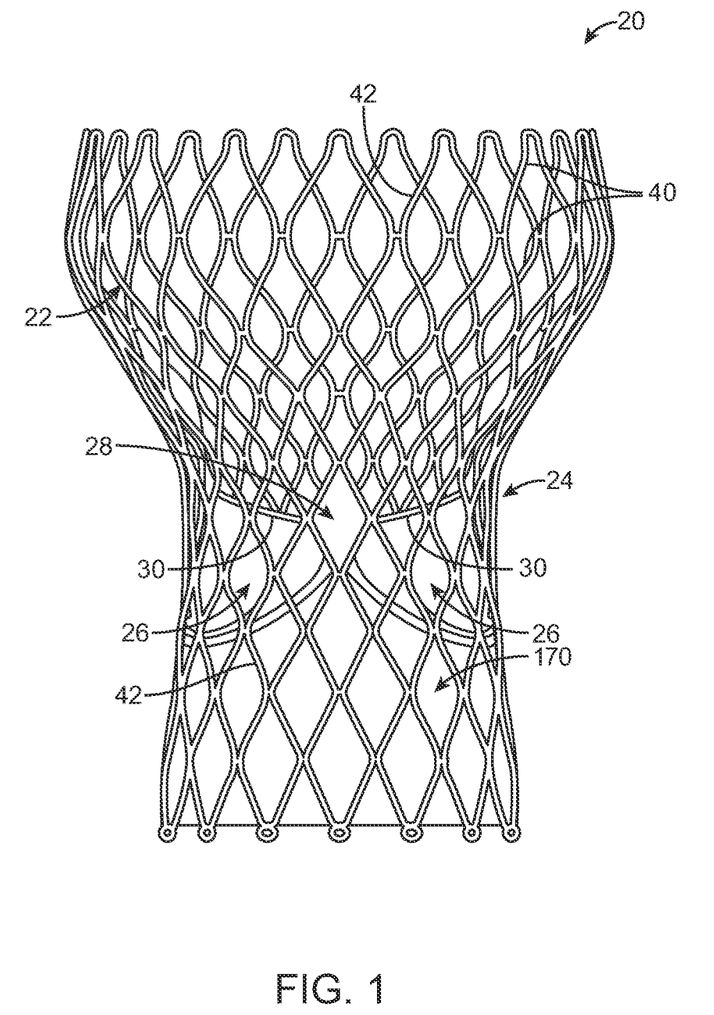
FIG. 1 is a simplified side view of a stented prosthetic heart valve in accordance with principles of the present disclosure.

One non-limiting example of a stented prosthetic heart valve 20 in accordance with principles of the present disclosure is shown FIG. 1, and includes a stent or stent frame 22 and a valve structure 24. The valve structure 24 is mounted to the stent 22, and provides two or more (typically three) leaflets 26. Construction of the leaflets 26 and assembly to the stent 22 are described in greater detail below. In general terms, however, the leaflets 26 are individually prepared and mounted to the stent 22 by a coupling apparatus 28 (one of which is schematically depicted in FIG. 1). Fastening of the leaflets 26 form commissural joints, with the unattached edges of the leaflets 26 forming coaptation edges 30 of the valve structure 24.

The stent 22 can assume a wide variety of forms, with FIG. 1 reflecting but one configuration envisioned by the present disclosure. The stent 22 is a tubular support structure that generally comprises a number of struts or wire portions 40 arranged relative to each other to provide a desired compressibility and strength to the prosthetic heart valve 20. In some embodiments, the struts 40 are arranged such that they are capable of self-transitioning from a compressed or collapsed arrangement to the normal, radially expanded or deployed arrangement shown. For example, a number of the struts 40 can be formed of a metal or similar material, and arranged such that the stent 22 allows for folding or compressing or crimping to the compressed arrangement in which an internal diameter defined by the stent 22 is smaller than the internal diameter when in the normal, expanded arrangement. The struts or wire portions 40 can be formed of platinum, stainless steel or other biocompatible metal or polymer. In some embodiments, a shape memory material such as a nickel titanium alloy (e.g., Nitinol™) is employed. With this material, the stent 22 is self-expandable from the compressed arrangement to the normal, expanded arrangement. In other embodiments, the stent 22 can be balloon-expandable from the compressed arrangement. The struts 40 can be defined by machining (e.g., laser-cutting, etching, etc.) the stent 22 from a metal tube; alternatively, the stent 22 can be fabricated using wire stock.

The stent 22, like most compressible and expandable cylindrical stents, generally takes the form of a series of zig-zag ring structures. The number of the struts or wire portions 40, the positioning of such struts, and various other features of the stent chosen can vary considerably from that shown in FIG. 1. Thus, the specifics of the stent 22 can vary widely, such that many other known, generally cylindrical stents may be used within the scope of the present disclosure. The series of zig-zag ring structures of the illustrated embodiment are coupled longitudinally to one another to form a generally cylindrical-shaped structure, although it is understood that the structures can be arranged in an at least slightly oval or elliptical shape. Further, a shape of the stent 22 can vary along a longitudinal length thereof as shown.

Figure 2:
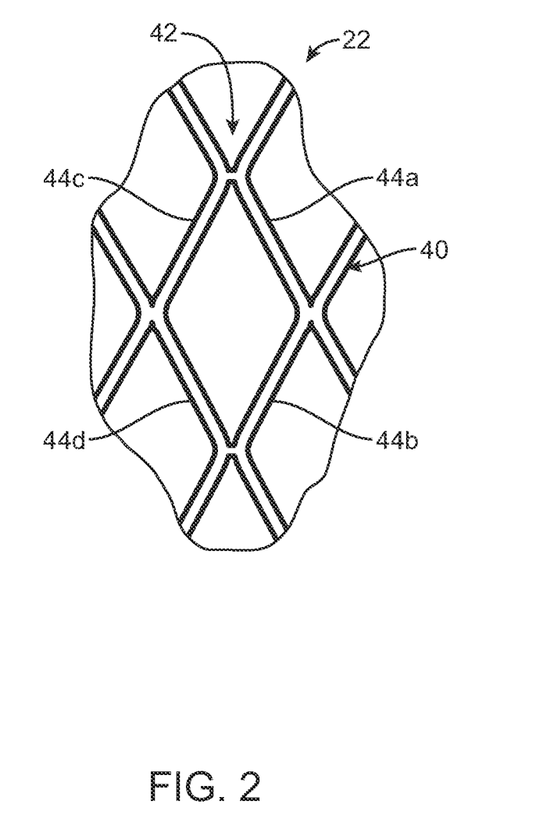
FIG. 2 is a enlarged view of a portion of a stent of the prosthetic heart valve of FIG. 1.

Regardless of an exact construction of the stent 22, the struts 40 combine to form a series of cells 42 (several of which are generally identified in FIG. 1). At least some of the cells 42 can have a diamond-like shape, with one such cell 42 being shown in greater detail in FIG. 2. The cell 42 is defined by strut segments 44a-44d, it being understood that two or more of the strut segments 44a-44d can be defined along the length of a single strut 40 (FIG. 1). The strut segments 44a-44d of the cells 42 provide regions for attachment of the leaflet assemblies 24 as described below.

Figure 3:
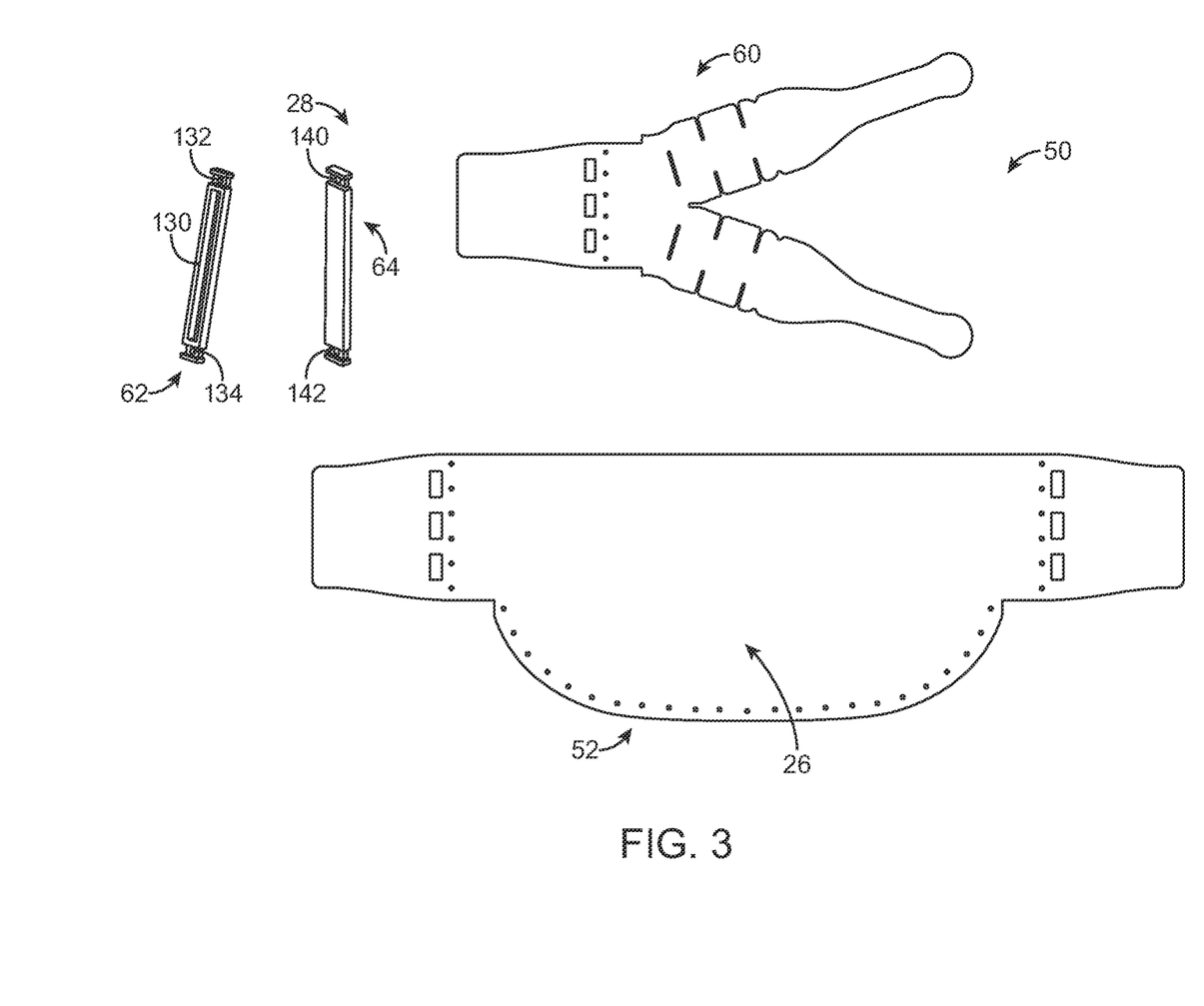
FIG. 3 is an exploded view of a leaflet assembly useful with the prosthetic heart valve of FIG. 1.

With the above understanding of the stent 22 in mind, each of the leaflets 26 are provided as part of a leaflet assembly 50, one embodiment of which is shown in FIG. 3. The leaflet assembly 50 includes at least one leaflet layer 52 and at least one of the coupling apparatuses 28. The leaflet layer 52 forms the leaflet 26. The coupling apparatus 28 connects the leaflet layer 52 to the stent 22 (FIG. 1) and includes at least one backing layer 60, a guide plate 62, and a pin 64. Details on the various components are provided below. In general terms, however, the backing layer 60 is coupled to the leaflet layer 52, with the guide plate 62 and pin 64 promoting fixation between the leaflet layer 52 and the backing layer 60, as well as with an additional, second leaflet layer 52. The backing layer 60, in turn, provides features for connection with the stent 22.

Figure 4:
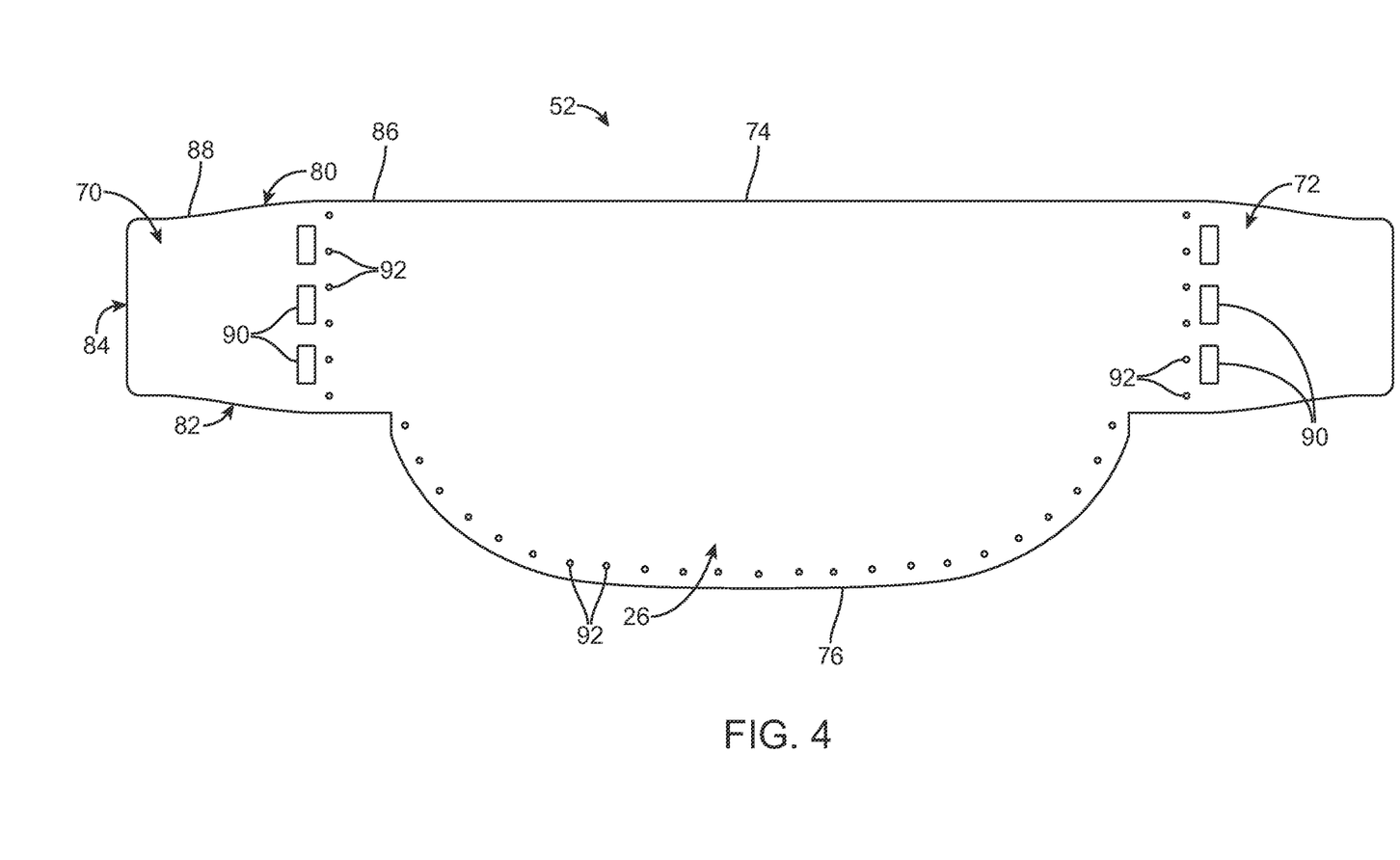
FIG. 4 is a top plan view of a leaflet layer useful with the assembly of FIG. 3.

The leaflet layer 52 is shown in greater detail in FIG. 4 (in flat form). The leaflet layer 52 can be formed or cut from a variety of materials, such as autologous tissue, xenograph material, or synthetics as are known in the art. Some materials for the leaflet layer 52 include mammalian tissue, such as porcine, equine or bovine pericardium, or a synthetic or polymeric material. In some embodiments, the leaflet layer 52 is a relatively flat sheet of pericardium material that can be obtained, for example, from a swine. It is understood that other donor species may alternatively be used or that the material used is not a pericardium material but instead is a different type of tissue or material, such as a polymer or bio-engineered film. The pericardium material may be at least partially fixed or cross-linked with a buffered gluteraldehyde solution or other solution at some point during the assembly process, in order to make the material easier for an operator to handle and manipulate. However, such treatments to the material are optional and may be different depending on operator preference, the material chosen, and the like.

The leaflet layer 52 in final form (e.g., following cutting and other processing) defines the leaflet 26 and opposing tab regions 70, 72. The leaflet 26 can be formed to a variety of shapes commensurate with a desired construction of the prosthetic heart valve 20 (FIG. 1), and defines a free edge 74 and a fixed edge 76 opposite the free edge 74. The free edge 74 forms one of the coaptation edges 30 (FIG. 1) of the finished valve structure 24 (FIG. 1). The tab regions 70, 72 project from opposite ends of the leaflet 26, and can have an identical shape. For example, a perimeter of the first tab region 70 is defined by opposing, first and second side edges 80, 82, and an end edge 84. The side edges 80, 82 project from the leaflet 26 and terminate at the end edge 84. In some embodiments, a direction of extension of the first side edge 80 is, at least in part, off-set or discontinuous with a plane of the free edge 74. More particularly, the first side edge 80 can be viewed as having a first segment 86 and a second segment 88. The first segment 86 extends from the free edge 74, and the second segment 88 extends from the first segment 86 to the end edge 84. In the exemplary embodiment shown, the first segment 86 is contiguous with the free edge 74, extending in the same plane as the free edge 74 (relative to the flat state of the leaflet layer 52 of FIG. 4). The second segment 88 extends from the first segment 86 at an angle that is non-parallel with, or as a deviation from the plane of, the free edge 74. Stated otherwise, the free edge 74 is arranged at a non-parallel angle relative to the second segment 88, with the second segment 88 projecting toward the second side edge 82 in extension to the end edge 84. As shown, the second side edge 82 can have a similar shape (e.g., at least a segment of the second side edge 82 projects toward the first side edge 80 in extension from the leaflet 26 to the end edge 84). The tab regions 70, 72 alternatively can have other perimeter shapes that may or may not include at least one segment that is discontinuous relative to a line or plane of the free edge 74.

In some embodiments, the leaflet layer 52 can include various features that facilitate subsequent assembly operations. For example, guide apertures 90 can be formed in each of the tab regions 70, 72 adjacent the leaflet 26 for reasons made clear below. Similarly, sewing holes 92 (referenced generally) can be provided along each of the tab regions 70, 72 and adjacent the fixed edge 76. The guide apertures 90 and sewing holes 92 can assume a variety of constructions, and other assembly-related features can also be provided. In other embodiments, some or all of the guide apertures 90 and the sewing holes 92 can be omitted.

Figure 5:
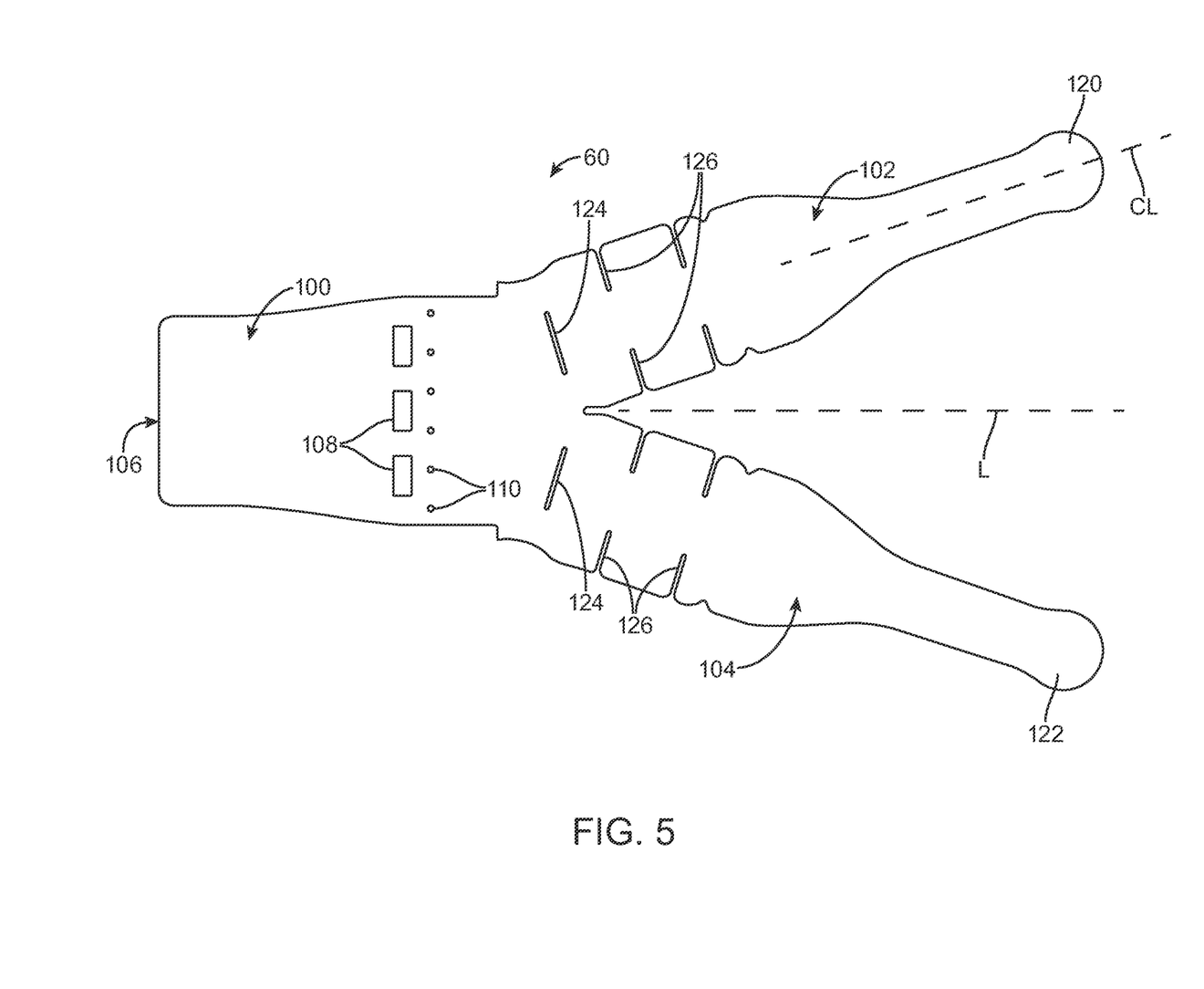
FIG. 5 is a top plan view of a backing layer useful with the assembly of FIG. 3.

One embodiment of the backing layer 60 is shown in FIG. 5. The backing layer 60 is formed of a thin, flexible yet structurally robust material, such as polyester or other synthetic, cloth-like material. The backing layer 60 is generally shaped as shown, defining a base 100, a first flap 102, and a second flap 104. The base 100 has a size and shape commensurate with that of the tab regions 70, 72 (FIG. 4) described above, and terminates at a leading edge 106. The base 100 is thus configured to "match" with one of the tab regions 70, 72, and can form corresponding guide apertures 108 and sewing holes 110.

The flaps 102, 104 extend from the base 100 opposite the leading edge 106 in an opposing, angular fashion, each terminating at a tip 120, 122. For example, a shape of the base 100 defines a longitudinal axis L, and a shape of the first flap 102 defines a center line CL; non-perpendicular and non-parallel projection of the first flap 102 from the base 100 is such that the center line CL and the longitudinal axis L form an angle in the range of 100 degrees-170 degrees. The second flap 104 has a similar relationship relative to the base 100, but at opposite side of the longitudinal axis L. For reasons made clear below, an angular relationship of the flaps 102, 104 relative to the base 100 correlates with geometric attributes of the leaflet layer 52 (FIG. 4), locating the flaps 102, 104 at a desired orientation relative to the free edge 74 (FIG. 4) upon final assembly. In some embodiments, the longitudinal axis L bi-sects the flaps 102, 104 such that the backing layer 60 is symmetrical about the longitudinal axis L. Alternatively, the backing layer 60 can have other shapes that facilitate the leaflet assembly techniques described below.

In some embodiments, a width of each of the flaps 102, 104 tapers in extension toward the corresponding tip 120, 122. Further, the tip 120, 122 can be rounded as shown. Finally, a receiving slot 124 can be formed within a perimeter of each of the flaps 102, 104, and folding slots 126 (referenced generally) can be formed along edges of each of the flaps 102, 104. As described below, these features promote mounting of the flaps 102, 104 to the stent 22 (FIG. 1). Other mounting features can alternatively be provided, and in other embodiments, one or more (including all) of the tapered shape, the rounded tip 120, 122, the receiving slot 124 and the folding slots 126 can be omitted.

Returning to FIG. 3, the guide plate 62 is an elongated, rigid body (e.g., surgically safe metal) defining a central passageway 130. The passageway 130 is sized and shaped in accordance with the size and shape of the tab regions 70, 72 (FIG. 3) and the backing layer base 100. Grooves 132, 134 are formed at opposite ends of the guide plate 62 for reasons made clear below.

The pin 64 is also an elongated, rigid body (e.g., surgically safe metal), and has a size and shape corresponding with the size and shape of the guide plate 62. The pin 64 need not include the central passageway 130 associated with the guide plate 62, but can form grooves 140, 142 at opposite ends thereof.

In some embodiments, construction of the leaflet assembly 50, and subsequent mounting to the stent 22 (FIG. 1), initially entails coupling two of the backing layers 60 with two of the leaflet layers 52. For example, FIG. 6 reflects an initial stage of fabrication of the leaflet assembly 50 in accordance with some embodiments of the present disclosure, and depicts two leaflet layers 52a, 52b placed directly against one another (it being understood that the second leaflet layer 52b is primarily hidden in the view of FIG. 6). A first backing layer 60a is arranged on and abuts an outer face of the first leaflet layer 52a (opposite the second leaflet layer 52b), and a second backing layer 60b (primarily hidden in FIG. 6) is arranged on and abuts an outer face of the second leaflet layer 52b (opposite the first leaflet layer 52a). Thus, the two tissue layers 52a, 52b are sandwiched between the two backing layers 60a, 60b. As reflected in FIG. 6, the first tab region 70a, 70b (referenced generally) of the leaflet layers 52a, 52b are aligned with another, and the base 100a, 100b of each of the backing layers 60a, 60b are aligned with the first tab regions 70a, 70b. The guide apertures 108 of the backing layers 60a, 60b and the guide apertures 90 (FIG. 4) of the leaflet layers 52a, 52b facilitate desired alignment between the layers 52a, 52b, 60a, 60b.

Figure 6:
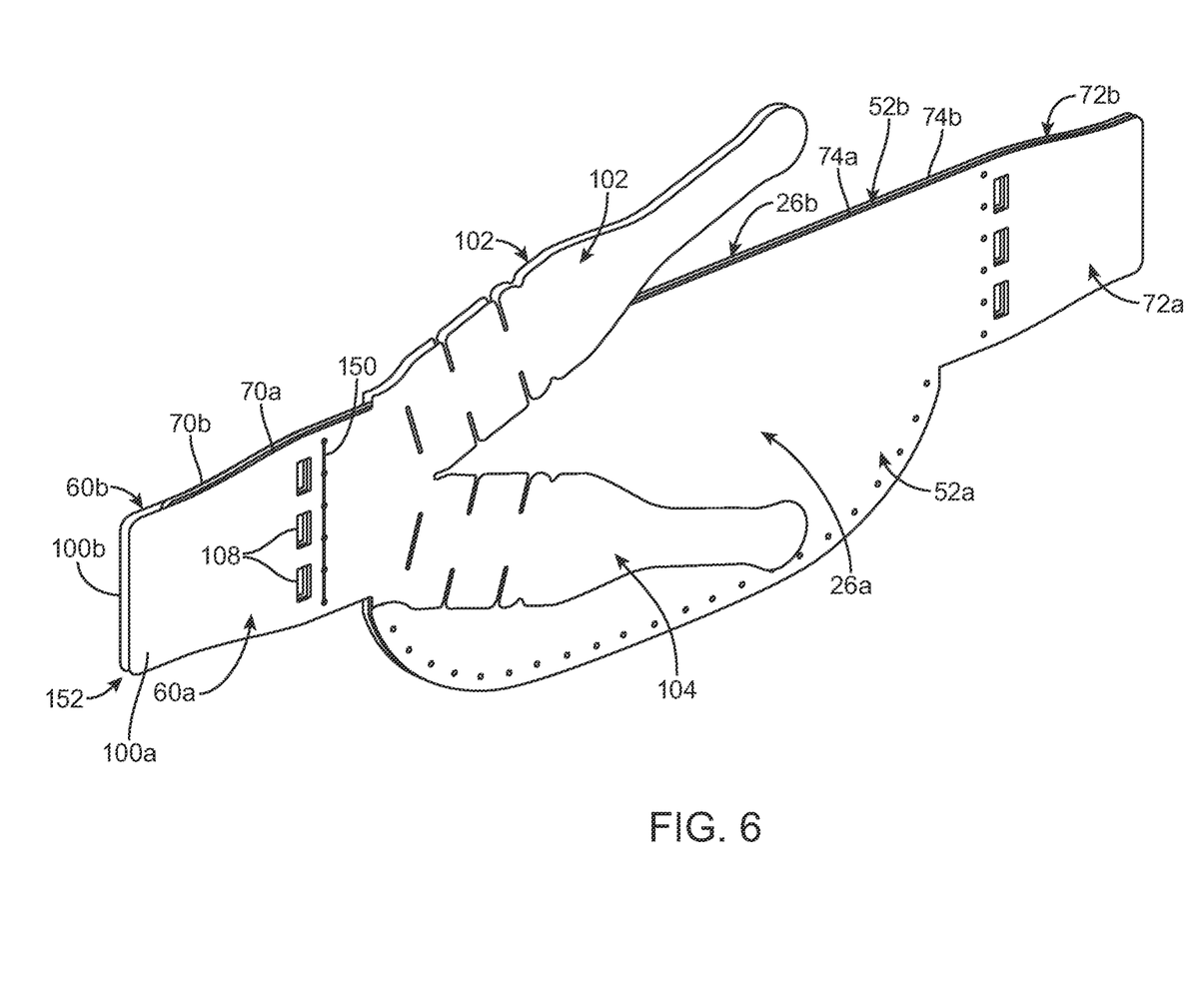
FIG. 6 is a perspective view illustrating assembly of two of the leaflet layers of FIG. 4 with two of the backing layers of FIG. 5.

Once arranged as described above, the leaflet layers 52a, 52b and the backing layers 60a, 60b are coupled to one another along a stitch line 150, for example by one or more sutures. Where provided, the leaflet layer sewing holes 92 (FIG. 4) and the backing layer sewing holes 110 (FIG. 5) can assist in forming the stitch line 150. Regardless, the leaflet layer first tab regions 70a, 70b and the backing layer bases 100a, 100b combine to define a tongue 152 (referenced generally). The flaps 102, 104 of both of the backing layers 60a, 60b project from the stitch line 150 opposite the tongue 152. Because the backing layer bases 100a, 100b have a shape commensurate with, and are aligned with, the first tab regions 70a, 70b, the flaps 102, 104 extend at an angle (non-parallel and non-perpendicular) relative to the free edge 74a, 74b of each leaflet 26a, 26b (in the flattened state shown).

As a point of reference, FIG. 6 shows the backing layers 60a, 60b being associated with the first tab region 70a, 70b of the leaflet layers 52a, 52b. The second tab region 72a, 72b of the first and second leaflet layers 52a, 52b are also illustrated as being aligned with one another. In some embodiments (e.g., a tri-leaflet prosthetic heart valve), the second tab regions 72a, 72b will be connected to a third tissue leaflet layer (not shown) and thus will not remain in the abutting relationship shown. Thus, it will be understood that several of the remaining Figures depict the leaflet layers 52a, 52b as aligned and abutting one another across their lengths (e.g., including at the second tab regions 72a, 72b) only for ease of illustration.

Figure 7A:
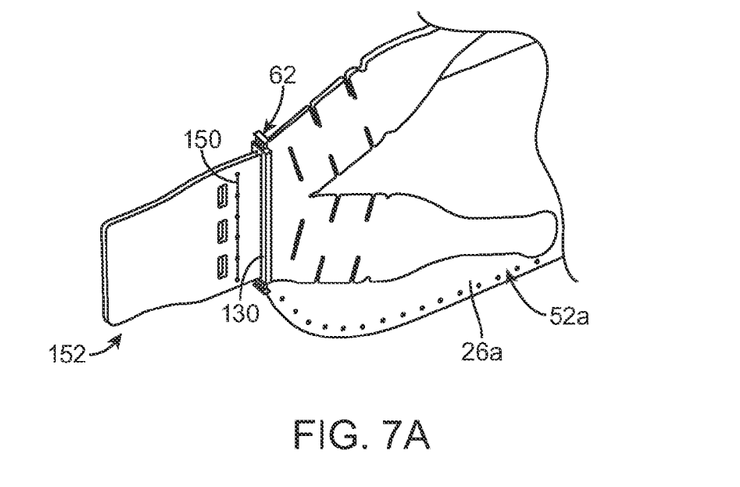
FIG. 7A-7F illustrate fabrication of the leaflet assembly of FIG. 3.
Figure 7B:
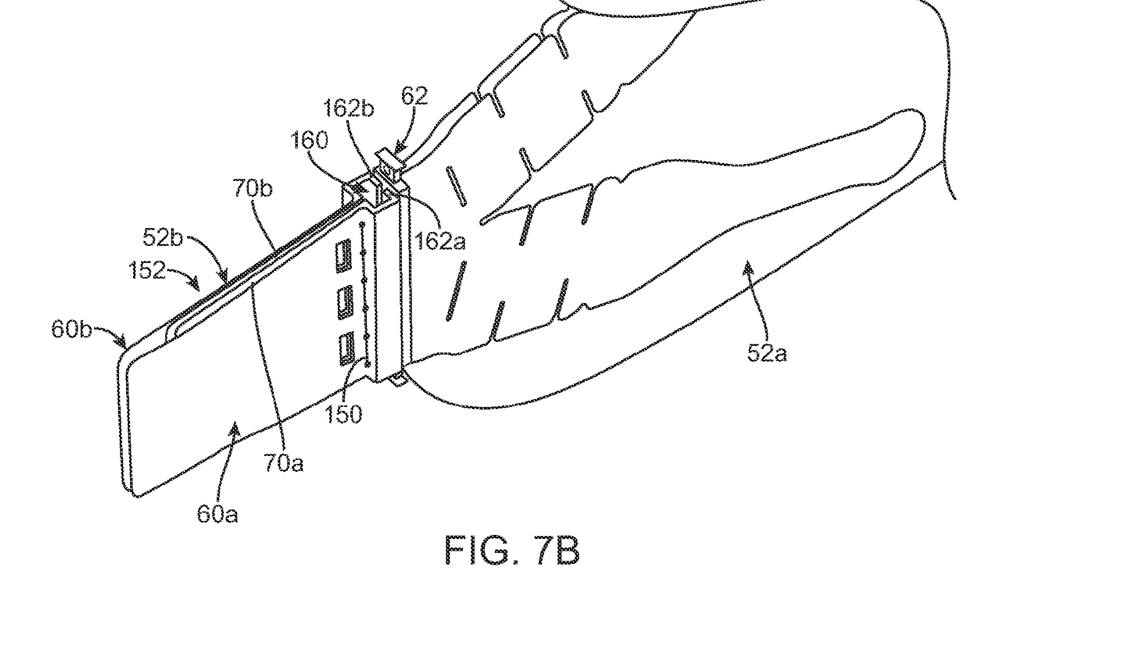
Figure 7C:
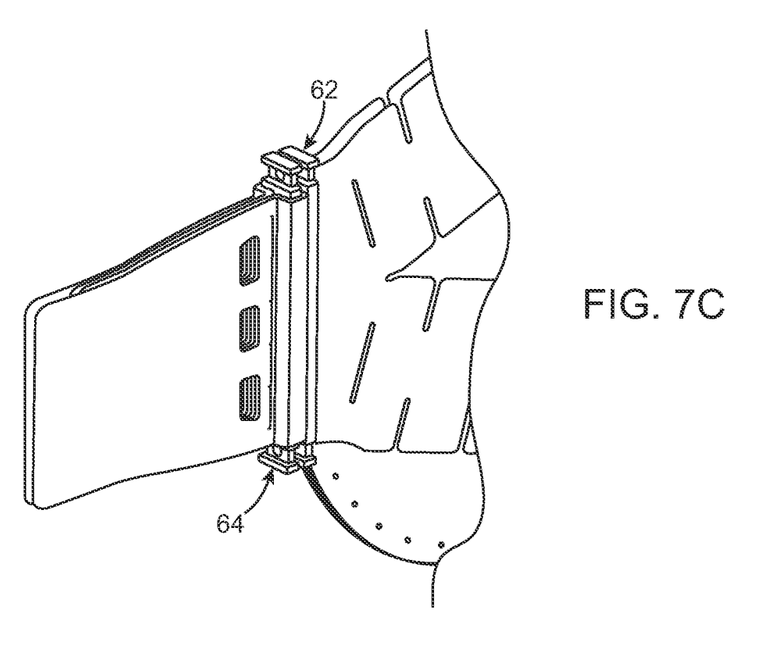
Figure 7D:
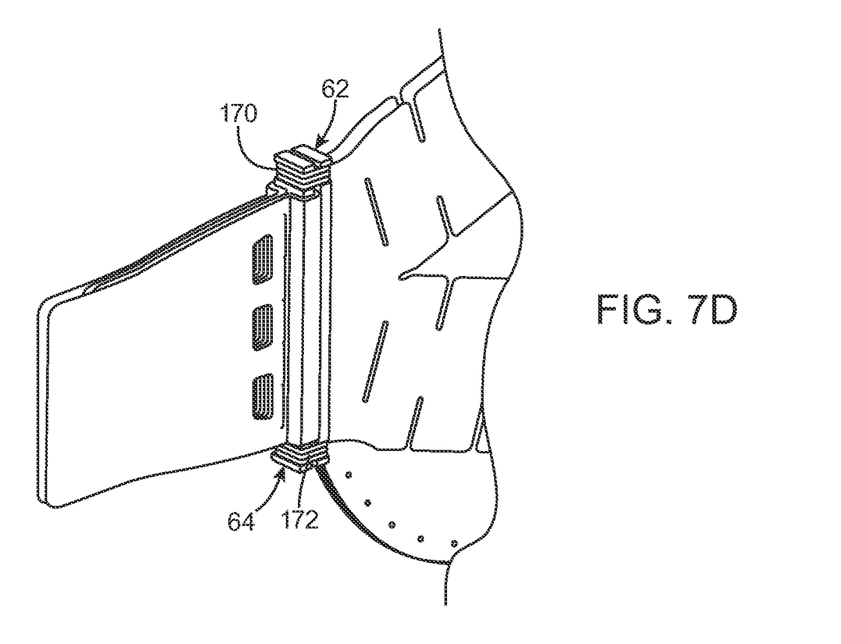

Turning to FIG. 7A, the tongue 152 is inserted through the passageway 130 of the guide plate 62 until the stitch line 150 is beyond the guide plate 62. In some embodiments, the guide plate 62 abuts the leaflets 26a, 26b. The tongue 152 is then manipulated to form a channel 160 between the first and second leaflet layers 52a, 52b as shown in FIG. 7B. For example, the tongue 152 can be manually pressed toward the guide plate 62, causing the tissue layers 52a, 52b, and in particular the first tab regions 70a, 70b, to separate from one another. The channel 160 is created between the stitch line 150 and the guide plate 62, and is generally sized and shaped to receive the pin 64 (FIG. 3). In this regard, the leaflet layers 52a, 52b are folded such that a segment 162a of the first leaflet layer 52a and a segment 162b of the second leaflet layer 52b exist between the channel 160 and the guide plate 62. FIG. 7C illustrates the pin 64 having been inserted into the channel 160 (FIG. 7B) and aligned with the guide plate 62. The guide plate 62 and the pin 64 are then secured to one another as shown in FIG. 7D. For examples, a first suture 170 can be employed to secure the guide plate 62 and the pin 64 at the corresponding grooves 132, 140 (FIG. 3), and a second suture 172 at the grooves 134, 142 (FIG. 3).

Figure 7E:
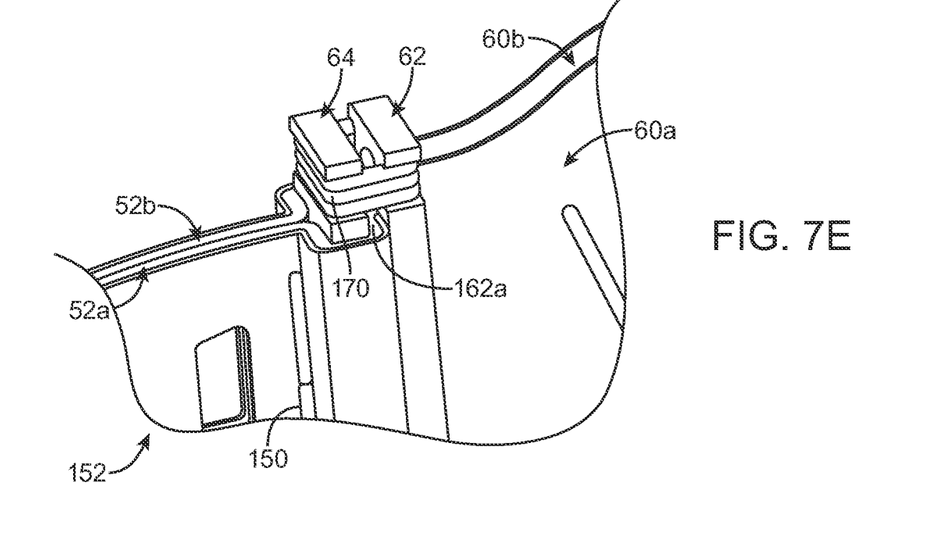
Figure 7F:
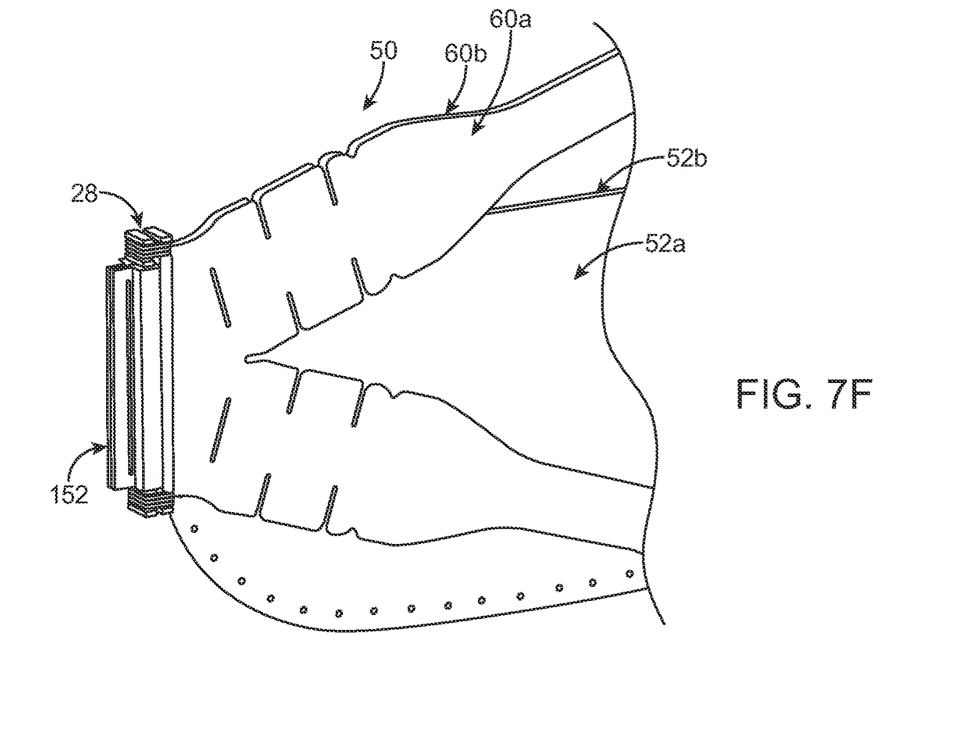

Upon final assembly, and with reference to FIG. 7E, the first and second leaflet layers 52a, 52b are robustly coupled to the guide plate 62 and the pin 64, and thus to one another. The first leaflet layer segment 162a is tightly pinched between the guide plate 62 and the pin 64, and is effectively held in place by friction. Though hidden in the view of FIG. 7E, the second leaflet layer segment 162b (FIG. 7B) is similarly tightly captured between the guide plate 62 and the pin 64. Excess material of the tongue 152 (beyond the stitch line 150) can be trimmed, resulting in the final leaflet assembly 50 construction of FIG. 7F. As shown, a small portion of the tongue 152 remains intact.

Figure 8:
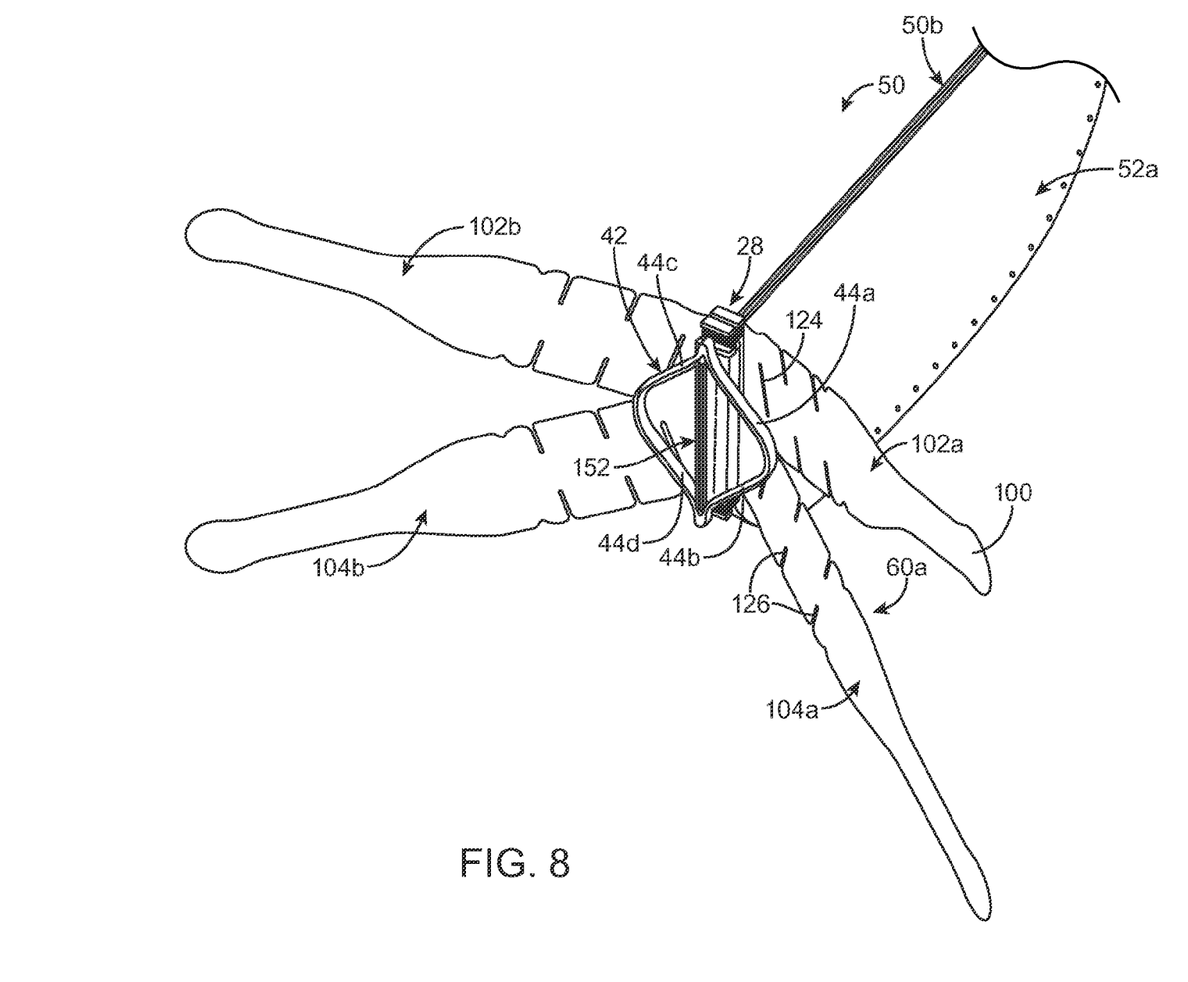

The leaflet assembly 50 can be mounted to the stent 22 (FIG. 1) via the coupling apparatus 28 in various fashions. In one embodiment, and as shown in FIG. 8, the tongue 152 is centrally aligned with one of the cells 42 formed by the stent 22. For ease of illustration, a single one of the stent cells 42 is shown in FIG. 8 (and thus the stent 22 is referenced generally in FIG. 8), it being understood that the stent 22 can take any of the forms described above. As a point of further clarification, the leaflet assembly 50 is arranged to extend across an interior of the stent 22 (thus, the view of FIG. 8 is relative to an exterior of the stent 22). The flaps 102, 104 of the first and second backing layers 60a, 60b are folded toward the stent 22 and then wrapped around a corresponding one of the strut segments 44a-44d. For example, the first flap 102a of the first backing layer 60a is wrapped around the first strut segment 44a; the second flap 104a of the first backing layer 60a is wrapped around the second strut segment 44b, etc. The wrapping technique employed for each of the flaps 102, 104 can be identical. With reference to the first flap 102a of the first backing layer 60a, the tip 120 is wrapped over the first strut segment 44a, inserted through the receiving slot 124, and pulled tight. Depending upon a length of the first flap 102, this wrapping operation can be repeated such that the first flap 102 forms two (or more) full turns around the first strut segment 44a. The folding slots 126 promote wrapping of the first flap 102a about the strut segment 44a, allowing the first flap 102a to more easily fold or deform. A similar process is employed for the remaining flaps 102, 104 relative to the corresponding strut segment 44b-44d.

Figure 9A:
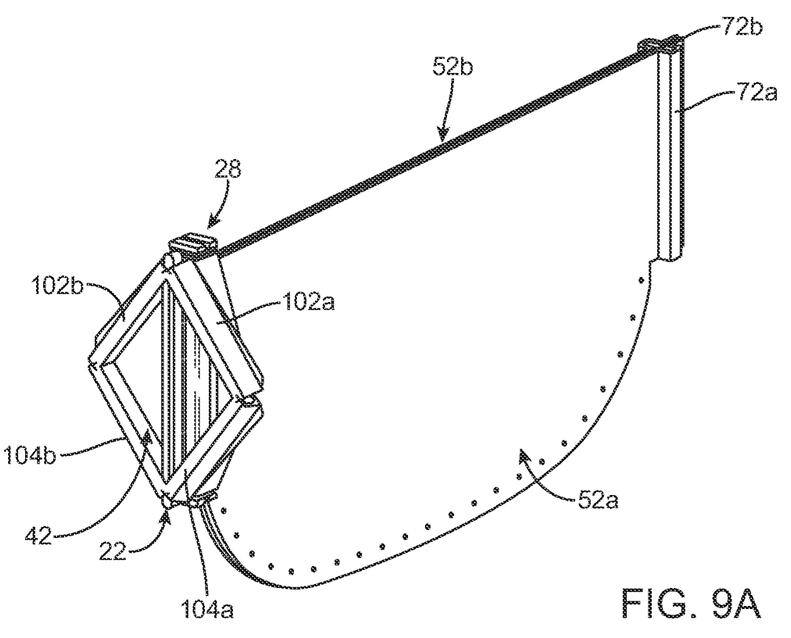
Figure 9B:
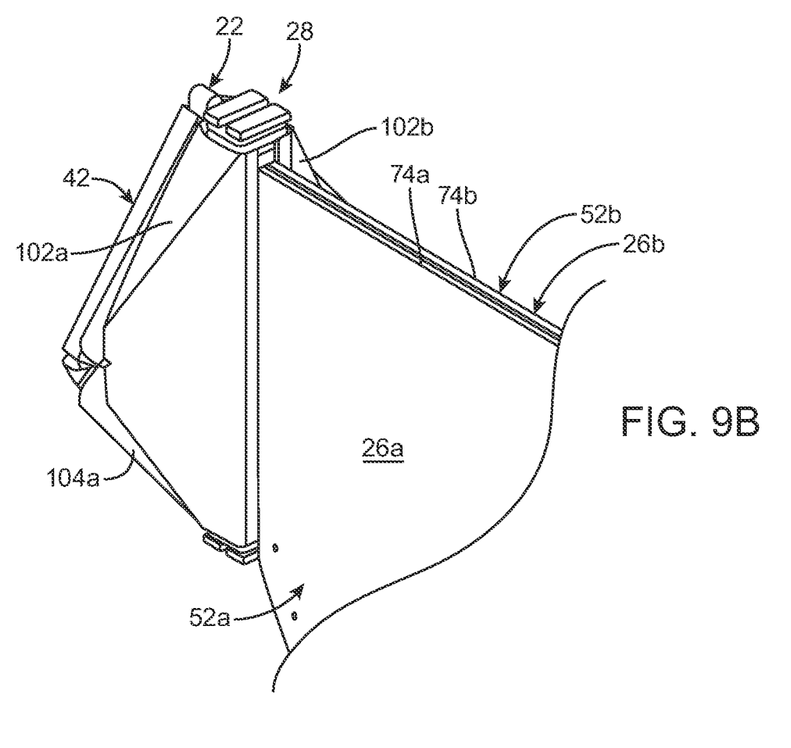

Final mounting of the coupling apparatus 28 to the stent 22 (and in particular the cell 42) is shown in FIGS. 9A and 9B. Any extra length of the flaps 102a-104b can be trimmed, and the flaps 102a-104b can be more robustly secured to the corresponding strut segment 44a-44d (FIG. 8) by sutures, glue or similar structures (not shown). As a point of reference, FIG. 9B illustrates the assembly from an interior of the stent 22, and reflects that the first and second leaflet layers 52a, 52b are held tightly to one another at a point of connection with the stent 22, and the free edges 74a, 74b of the leaflets 26a, 26b are aligned. Further, the free edges 74a, 74b are maintained at an angle off-set from the spatial orientations of the strut segments 44a-44d.

Figure 10:
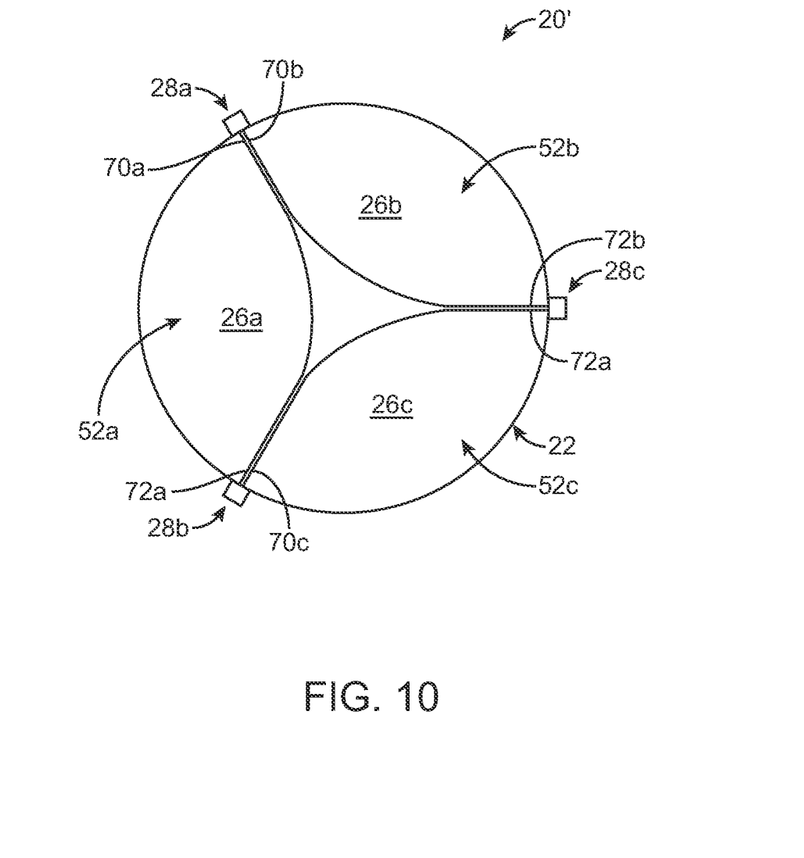
FIG. 10 is a simplified top view of a stented prosthetic heart valve fabricated in accordance with methods of the present disclosure.

Though not shown in FIG. 9A, the opposite, second tab region 72a, 72b of the first and second leaflet layers 52a, 52b can be similarly connected to another cell of the stent (via another coupling apparatus 28). Alternatively, one or more additional leaflet layers can be provided, and connection to the stent 22 provided with additional ones of the coupling apparatuses 28. For example, FIG. 10 is a simplified end view of an embodiment stented prosthetic heart valve 20' upon final assembly and including the leaflet layers 52a, 52b mounted to the stent 22 by a first coupling apparatus 28a as described above. A third leaflet layer 52c is also provided, with the stented prosthetic heart valve 20' being configured as a tri-leaflet valve (i.e., three of the leaflets 26a-26c are provided). The second tab region 72a of the first leaflet layer 52a is attached to a first tab region 70c of the third leaflet layer 52c by a second coupling apparatus 28b that is also secured to the stent 22. The second end tab region 72b of the second leaflet layer 52b is attached to a second tab region 72c of the third leaflet layer 52c by a third coupling apparatus 28c that is also secured to the stent 22. The points of connection to the stent 22 serve as commissures for the resultant valve structure 24'. In this regard, the cells 44 (not shown in FIG. 10, but see, for example, FIG. 2) to which the respective coupling apparatuses 28a-28c are mounted can be formatted differently from other cells or structures of the stent 22 to more directly indicate a desired location of the commissures.

Returning to FIG. 1, stented prosthetic heart valves of the present disclosure can optionally include one or more additional components known in the art. For example, with the one exemplary embodiment shown, the stented prosthetic heart valve 20 includes a skirt 170. Where provided, the skirt 170 can be cut from a sheet of animal pericardial tissue akin to the tissue employed for the tissue leaflet layers 52, and is joined to the stent 22 in a conventional fashion. The leaflets 26 are joined to the skirt 170 in known fashions, such as sewing or glue (e.g., via the sewing holes 92 (FIG. 4) described above). Other stent structures can be connected to the stent 22, a conventional sewing ring can be formed, etc. Further, the stented prosthetic heart valves of the present disclosure can optionally include various features that facilitate temporary connection to a delivery tool or system.

The stented prosthetic heart valves and corresponding methods of manufacture of the present disclosure provide a marked improvement over previous designs. Adjacent leaflets are tightly maintained in an aligned relationship with one another, and are held to the stent by a coupling apparatus that is easy for an operator to handle and manipulate. Further, the coupling apparatus accounts for the angular differences between the strut segments forming a cell of the stent to which the leaflets are attached, locating the leaflet free edge at a desired spatial orientation.

Although the present disclosure has been described with reference to preferred embodiments, workers skilled in the art will recognize that changes can be made in form and detail without departing from the spirit and scope of the present disclosure.

What is claimed is:

1. A stented prosthetic valve comprising:
   a stent including a plurality of struts combining to define a tubular body, the plurality of struts forming first and second strut segments;
   a plurality of leaflets mounted to the stent, a first one of the leaflets being provided as part of a first leaflet layer having a first tab region; and
   a first coupling apparatus for connecting the first leaflet layer to the stent, the first coupling apparatus including:
   a first backing layer,
   a guide plate apart from the stent,
   a pin apart from the stent,
   wherein a portion of the backing layer and the first tab region are captured between the guide plate and the pin;
   wherein the backing layer is attached to at least one of the first and second strut segments to mount the first leaflet to the stent;
   wherein the backing layer includes a base and a first flap projecting from the base, and further wherein the base abuts the first tab region at an interface established between the guide plate and the pin, and even further wherein the first flap projects from the interface and is wrapped about the first strut segment;
   wherein the backing layer further includes a second flap projecting from the base, and further wherein the second flap is wrapped about the second strut segment.

2. The stented prosthetic valve of claim 1, wherein the backing layer is attached to a commissure region defined by the stent.

3. The stented prosthetic valve of claim 1, wherein the guide plate forms a passageway, and further wherein the first tab region and the backing layer extend through the passageway.

4. The prosthetic valve of claim 1, wherein the first tab region and the backing layer are frictionally held between the guide plate and the pin.

5. The prosthetic valve of claim 4, wherein the first coupling apparatus further includes a first suture affixing the guide plate to the support pin, the first suture being free of the stent, the first tab region and the backing layer.

6. The prosthetic valve of claim 1, wherein the first coupling apparatus further includes a second backing layer, and further wherein the first tab region is disposed between the first and second backing layers.

7. The prosthetic valve of claim 6, wherein the second backing layer includes a base and a first flap, and further wherein:
   the first tab region is disposed between the base of the first backing layer and the base of the second backing layer; and
   the first flap of the second backing layer is wrapped about a third strut segment.

8. The prosthetic valve of claim 7, wherein the first and second backing layers each further include a second flap projecting from the corresponding base, and further wherein the second flap of the second backing layer is wrapped about a fourth strut segment.

9. The prosthetic valve of claim 1, wherein the plurality of leaflets further includes a second leaflet provided as part of a second leaflet layer having a first tab region, and the first coupling apparatus further includes a second backing layer, the backing layers each including a base and a flap, and further wherein the first tab region of the first and second leaflet layers are disposed between the base of the first backing layer and the base of the second backing layer.

10. The prosthetic valve of claim 9, wherein the guide plate forms a passageway, and further wherein the first tab regions and the bases collectively define a tongue extending through the passageway, including the first backing layer abutting the first leaflet layer, the second leaflet layer abutting the first leaflet layer opposite the first backing layer, and the second backing layer abutting the second leaflet layer opposite the first leaflet layer.

11. The prosthetic valve of claim 10, wherein the pin is disposed between the first and second leaflet layers adjacent the guide plate.

12. The prosthetic valve of claim 11, wherein the guide plate is connected to the pin to frictionally secure the backing layers and the leaflet layers between the guide plate and the support pin.

13. The prosthetic valve of claim 9, wherein the plurality of leaflets further includes a third leaflet provided as part of a third leaflet layer having a first tab region, wherein each of the first, second and third leaflet layers each including a second tab region opposite the corresponding first tab region, the prosthetic valve further including second and third coupling apparatuses each including a backing layer, and further wherein:
   the first coupling apparatus connects the first tab region of the first leaflet layer and the first tab region of the second leaflet layer to the stent, including a flap of the backing layer of the first coupling apparatus wrapped about a first strut segment;
   the second coupling apparatus connects the second tab region of the first leaflet layer and the first tab region of the third leaflet layer to the stent, including a flap of the backing layer of the second coupling apparatus wrapped about a second strut segment; and
   the third coupling apparatus connects the second tab region of the second leaflet layer and the second tab region of the third leaflet layer to the stent, including a flap of the backing layer of the third coupling apparatus wrapped about a third strut segment.

14. The prosthetic valve of claim 1, wherein the backing layer is a polyester material.

15. The stented prosthetic heart valve of claim 7, wherein the plurality of leaflets further includes a second leaflet layer having a first tab region;
  wherein the respective tab regions of the first and second leaflet layers are affixed between the bases of the first and second backing layers;
  and further wherein the flaps of the first backing layer and the flap of the second backing layer do not overlap, the first and second strut segments combining to form a portion of a cell of the stent.

16. The prosthetic valve of claim 1, wherein the backing layer is wrapped about one of the first and second strut segments at least two full turns.

17. The prosthetic valve of claim 1, wherein the backing layer defines a receiving slot, and further wherein the first flap is wrapped about the first strut segment and passes through the receiving slot.

18. The prosthetic valve of claim 1, wherein relative to a central axis defined by the stent the pin is radially outward of the guide plate, and the first strut segment is radially outward of the pin.

* * * * *